(12) United States Patent
Louwagie et al.

(10) Patent No.: US 12,011,606 B2
(45) Date of Patent: Jun. 18, 2024

(54) INTERMEDIATE MEMBER WITH PROTRUSIONS FOR MEDICAL DEVICE BATTERY ASSEMBLIES

(71) Applicant: Medtronic, Inc., Minneapolis, MN (US)

(72) Inventors: Jeffrey J. Louwagie, Minnetonka, MN (US); Joseph J. Viavattine, Vadnais Heights, MN (US); Richard W. Swenson, Edina, MN (US); Jason P. Weiand, Lake Elmo, MN (US)

(73) Assignee: Medtronic, Inc., Minneapolis, MN (US)

( * ) Notice: Subject to any disclaimer, the term of this patent is extended or adjusted under 35 U.S.C. 154(b) by 41 days.

(21) Appl. No.: 17/097,903

(22) Filed: Nov. 13, 2020

(65) Prior Publication Data

US 2021/0196961 A1 Jul. 1, 2021

Related U.S. Application Data

(60) Provisional application No. 62/955,556, filed on Dec. 31, 2019.

(51) Int. Cl.
| | | |
|---|---|---|
| *A61N 1/378* | (2006.01) | |
| *H01M 10/654* | (2014.01) | |
| *H01M 10/658* | (2014.01) | |

(52) U.S. Cl.
CPC .......... *A61N 1/378* (2013.01); *H01M 10/654* (2015.04); *H01M 10/658* (2015.04); *H01M 2220/30* (2013.01)

(58) Field of Classification Search
CPC .. A61N 1/378; A61N 1/37512; A61N 1/3758; A61N 1/375; H01M 10/654; H01M 10/658; H01M 2220/30; H01M 10/425; H01M 50/103; H01M 50/117; H01M 50/121; H01M 50/131; H01M 50/14; Y02E 60/10
See application file for complete search history.

(56) References Cited

U.S. PATENT DOCUMENTS

| | | |
|---|---|---|
| 7,294,432 B2 | 11/2007 | Howard et al. |
| 7,544,220 B2 | 6/2009 | Zhao et al. |
| 7,927,738 B2 | 4/2011 | Howard et al. |
| 8,623,548 B2 | 1/2014 | Kim et al. |
| 8,932,751 B2 | 1/2015 | Jeon |
| 8,962,167 B2 | 2/2015 | Kim et al. |

(Continued)

OTHER PUBLICATIONS

U.S. Appl. No. 16/841,157, filed Apr. 6, 2020, by Louwagie et al.

(Continued)

*Primary Examiner* — Nathanael T Zemui
(74) *Attorney, Agent, or Firm* — Shumaker & Sieffert, P.A.

(57) ABSTRACT

In some examples, a battery assembly for an implantable medical device. The assembly includes a housing, an electrode stack comprising a plurality of electrode plates disposed inside the housing, and an intermediate member configured to align the electrode stack at a fixed position within the housing, the intermediate member comprising a plurality of side walls, and at least one protrusion disposed on an exterior surface of the side walls, wherein the at least one protrusion is in thermal contact with an interior surface of the housing.

15 Claims, 11 Drawing Sheets

(56) References Cited

U.S. PATENT DOCUMENTS

| | | | |
|---|---|---|---|
| 9,029,007 B2 | 5/2015 | Hyung | |
| 9,190,634 B2 | 11/2015 | Jeon | |
| 9,203,074 B2 | 12/2015 | Seong et al. | |
| 2007/0231681 A1* | 10/2007 | Casby | H01G 9/14 429/185 |
| 2008/0000882 A1 | 1/2008 | VanDerlick | |
| 2013/0011714 A1 | 1/2013 | Han et al. | |
| 2014/0356685 A1* | 12/2014 | Okuda | H01M 10/6554 429/120 |
| 2015/0196867 A1* | 7/2015 | Ries | H01M 10/4264 429/57 |
| 2015/0214585 A1* | 7/2015 | Sun | H01M 50/51 429/120 |
| 2016/0293995 A1 | 10/2016 | Pasma et al. | |

OTHER PUBLICATIONS

U.S. Appl. No. 16/426,849, filed May 30, 2019, by Zhao et al.
U.S. Appl. No. 16/530,470, filed Aug. 2, 2019, by Zhao.
International Search Report and Written Opinion of International Application No. PCT/US2020/061430, dated Mar. 4, 2021, 12 pp.

* cited by examiner

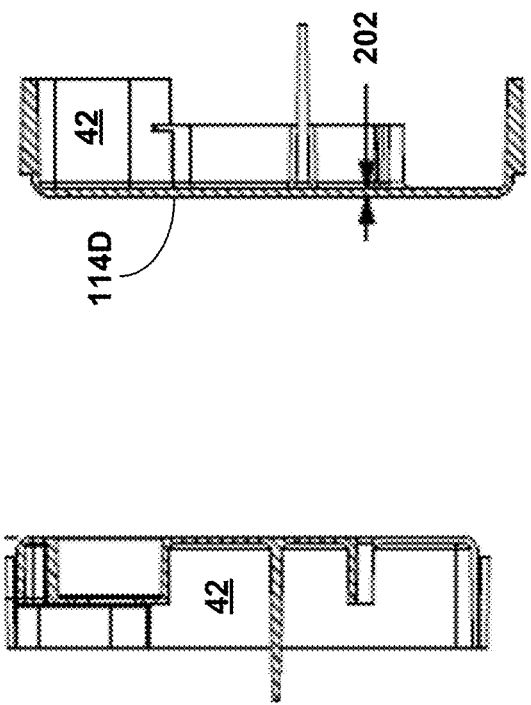
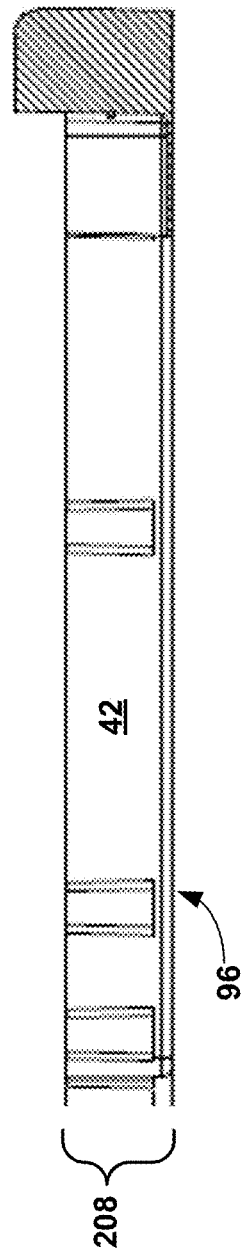
FIG. 8A
FIG. 8B
FIG. 8C

INTERMEDIATE MEMBER WITH PROTRUSIONS FOR MEDICAL DEVICE BATTERY ASSEMBLIES

This application claims the benefit of U.S. Provisional Patent Application No. 62/955,556, filed Dec. 31, 2019, the entire content being incorporated herein by reference.

TECHNICAL FIELD

The disclosure relates to batteries, such as batteries of medical devices.

BACKGROUND

Medical devices such as implantable medical devices (IMDs) include a variety of devices that deliver therapy (such as electrical simulation or drugs) to a patient, monitor a physiological parameter of a patient, or both. IMDs typically include a number of functional components encased in a housing. The housing is implanted in a body of the patient. For example, the housing may be implanted in a pocket created in a torso of a patient. The housing may include various internal components such as batteries and capacitors to deliver energy for therapy delivered to a patient and/or to power circuitry for monitoring a physiological parameter of a patient and controlling the functionality of the medical device.

SUMMARY

In some aspects, the disclosure is directed to battery assemblies for use, e.g., in a medical device, and techniques for manufacturing the battery assemblies.

In one example, the disclosure is directed to a battery assembly. The assembly may include a housing; an electrode stack comprising a plurality of electrode plates disposed inside the housing; and an intermediate member configured to align the electrode stack at a fixed position within the housing, the intermediate member having a plurality of side walls; and at least one protrusion disposed on an exterior surface of the plurality of side walls, wherein the at least one protrusion is in thermal contact with an interior surface of the housing.

In another example, the disclosure is directed to an implantable medical device (IMD) including an outer housing; processing circuitry; and a battery assembly within the outer housing, the battery assembly including: a battery housing; an electrode stack comprising a plurality of electrode plates disposed inside the housing; and an intermediate member configured to align the electrode stack at a fixed position within the housing, the intermediate member including: a plurality of side walls; and at least one protrusion disposed on an exterior surface of the side walls, wherein the at least one protrusion is in thermal contact with an interior surface of the housing; wherein the processing circuitry is configured to control delivery of electrical therapy from the IMD to a patient using power supplied by the battery assembly.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIGS. 8A-8C are cross-sectional views of the intermediate member of FIGS. 7A and 7B.

DETAILED DESCRIPTION

Figure 1:
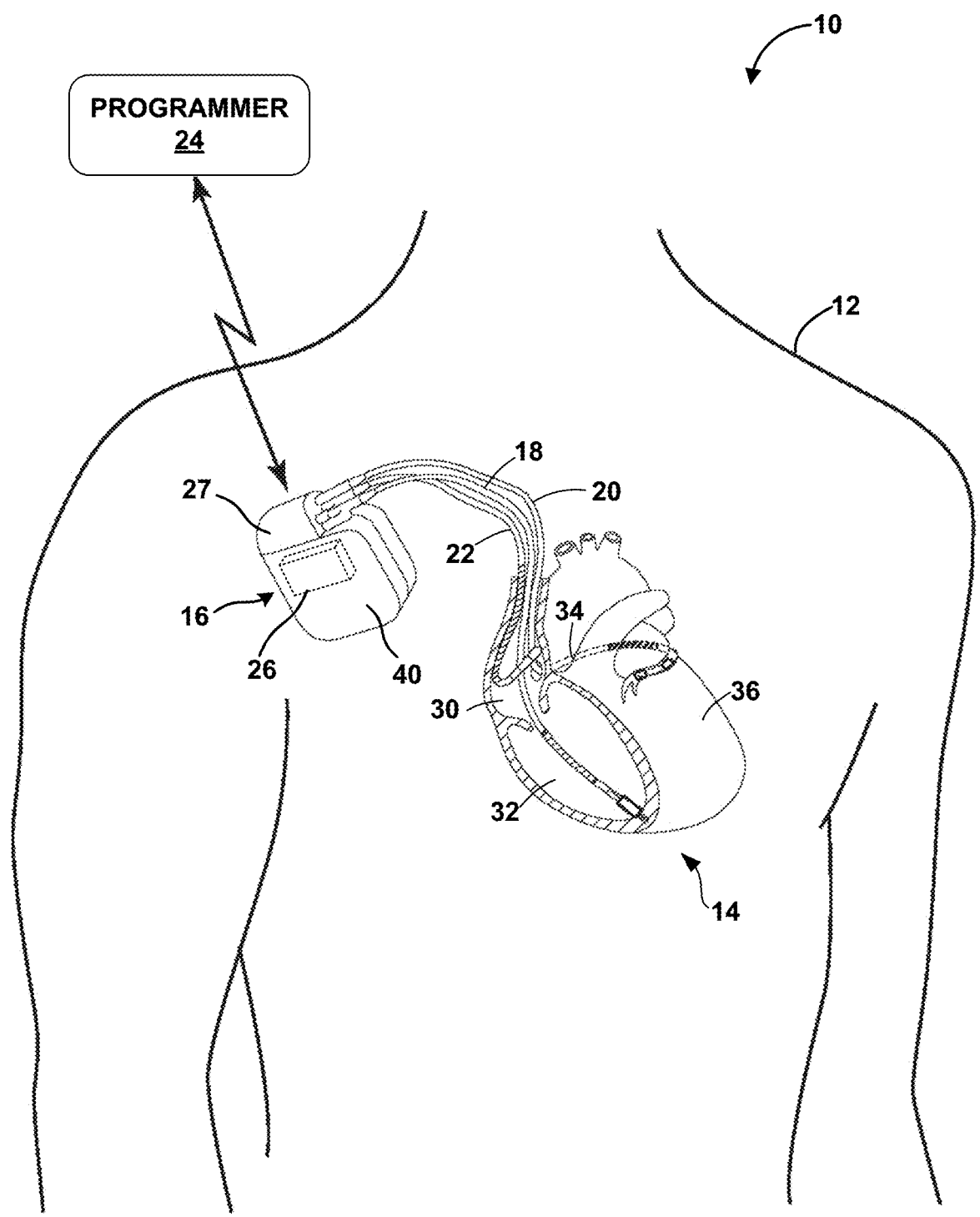
FIG. 1 is a conceptual diagram that illustrates an example medical device system that may be used to deliver therapy to a patient.

A variety of medical devices may utilize one or more batteries as a power source for operational power. For example, an implantable medical device (IMD) that provides cardiac rhythm management therapy to a patient may include a battery to supply power for the generation of electrical therapy or other functions of the IMD. For ease of illustration, examples of the present disclosure will be described primarily with regard to batteries employed in IMDs that provide cardiac-rhythm management therapy. However, as will be apparent from the description herein, examples of the disclosure are not limited to IMDs that provide such therapy. For example, in some instances, one or more of the example batteries described herein may be used by a medical device configured to deliver electrical stimulation to a patient in the form of neurostimulation therapy (e.g., spinal cord stimulation therapy, deep brain stimulation therapy, peripheral nerve stimulation therapy, peripheral nerve field stimulation therapy, pelvic floor stimulation therapy, and the like). In some examples, example batteries of this disclosure may be employed in medical device configured to monitor one or more patient physiological parameters, e.g., by monitoring electrical signals of the patient, alone or in conjunction with the delivery of therapy to the patient.

In the assembly process for some battery assemblies, two or more components, such as of an external housing, may be welded together. During the welding process, a relatively large amount of heat energy may be incidentally transferred to more heat-sensitive components internal to the battery. Accordingly, typical assembly processes may be forced to use a lower-heat welding process, resulting in less-robust welded joints. In other examples, the assembly process may take significantly longer to complete, in order to ensure that internal components have not been damaged during the welding.

In accordance with at least some examples of the disclosure, a battery assembly for a medical device includes a polymeric intermediate member configured to position (e.g., align) an electrode stack within an external battery housing. The intermediate member may define a plurality of side walls surrounding the electrode stack. The side walls of the intermediate member may define one or more protrusions configured to contact an internal surface of the battery housing. The protrusions may provide multiple technical advantages, including creating an insulation gap between the intermediate member and the battery housing, as well as absorbing heat transferred from the battery housing, preventing the rest of the intermediate member from melting and/or deforming, such as due to welding during an assembly process. In this way, the techniques of this disclosure provide a number of technical advantages. For example, the insulating and positioning protrusions of the intermediate member may allow for reduced production times and productions costs of the battery by ensuring that more critical components of the battery are not melting, deforming, or otherwise overheating during the welding process. For example, protrusions 52 can be designed with added mass in order to sustain more thermal energy transfer before attaining the melting temperature of the polymer. Accordingly, the protrusions may allow for the use of higher weld energy (e.g., heat) during the assembly process, and thereby allow for more robust weld joints in the hermetic enclosure. In some examples, the inclusion of protrusions 52 may improve the accuracy or reduce the duration of the injection-molding process of intermediate member 42. For example, during the injection-molding process, protrusions 52 may function as molten-plastic supply pathways, enabling the molten plastic to access and fill other fine or narrow regions of intermediate member 42.

FIG. 1 is a conceptual diagram that illustrates an example medical device system 10 that may be used to provide electrical therapy to a patient 12. Patient 12 ordinarily, but not necessarily, will be a human. System 10 may include an IMD 16, and an external device 24. In the example illustrated in FIG. 1, IMD 16 has battery 26 positioned within an outer housing 40 of the IMD 16. Battery 26 may be a primary or secondary battery.

While the examples in the disclosure are primarily described with regard to battery 26 positioned within housing 40 of IMD 16 for delivery of electrical therapy to heart of patient 12, in other examples, battery 26 may be utilized with other implantable medical devices. For example, battery 26 may be utilized with an implantable drug delivery device, an implantable monitoring device that monitors one or more physiological parameters of patient 12, an implantable neurostimulator (e.g., a spinal cord stimulator, a deep brain stimulator, a pelvic floor stimulator, a peripheral nerve stimulator, or the like), or the like. Moreover, while examples of the disclosure are primarily described with regard to implantable medical devices, examples are not limited as such. Rather, some examples of the batteries described herein may be employed in any medical device including non-implantable medical devices. For example, an example battery may be employed to supply power to a medical device configured delivery therapy to a patient externally or via a transcutaneoulsy implanted lead or drug delivery catheter.

In the example depicted in FIG. 1, IMD 16 is connected (or "coupled") to leads 18, 20, and 22. IMD 16 may be, for example, a device that provides cardiac rhythm management therapy to heart 14, and may include, for example, an implantable pacemaker, cardioverter, and/or defibrillator that provides therapy to heart 14 of patient 12 via electrodes coupled to one or more of leads 18, 20, and 22. In some examples, IMD 16 may deliver pacing pulses, but not cardioversion or defibrillation shocks, while in other examples, IMD 16 may deliver cardioversion or defibrillation shocks, but not pacing pulses. In addition, in further examples, IMD 16 may deliver pacing pulses, cardioversion shocks, and defibrillation shocks.

IMD 16 may include electronics and other internal components necessary or desirable for executing the functions associated with the device. In one example, IMD 16 includes one or more of processing circuitry, memory, a signal generation circuitry, sensing circuitry, telemetry circuitry, and a power source. In general, memory of IMD 16 may include computer-readable instructions that, when executed by a processor of the IMD, cause it to perform various functions attributed to the device herein. For example, processing circuitry of IMD 16 may control the signal generator and sensing circuitry according to instructions and/or data stored on memory to deliver therapy to patient 12 and perform other functions related to treating condition(s) of the patient with IMD 16.

IMD 16 may include or may be one or more processors or processing circuitry, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" and "processing circuitry" as used herein may refer to any of the foregoing structure or any other structure suitable for implementation of the techniques described herein.

Memory may include any volatile or non-volatile media, such as a random-access memory (RAM), read only memory (ROM), non-volatile RAM (NVRAM), electrically erasable programmable ROM (EEPROM), flash memory, and the like. Memory may be a storage device or other non-transitory medium.

The signal generation circuitry of IMD 16 may generate electrical therapy signals that are delivered to patient 12 via electrode(s) on one or more of leads 18, 20, and 22, in order to provide pacing signals or cardioversion/defibrillation shocks, as examples. The sensing circuitry of IMD 16 may monitor electrical signals from electrode(s) on leads 18, 20, and 22 of IMD 16 in order to monitor electrical activity of heart 14. In one example, the sensing circuitry may include switching circuitry to select which of the available electrodes on leads 18, 20, and 22 of IMD 16 are used to sense the heart activity. Additionally, the sensing circuitry of IMD 16 may include multiple detection channels, each of which includes an amplifier, as well as an analog-to-digital converter for digitizing the signal received from a sensing channel (e.g., electrogram signal processing by processing circuitry of the IMD).

Telemetry circuitry of IMD 16 may be used to communicate with another device, such as external device 24. Under the control of the processing circuitry of IMD 16, the telemetry circuitry may receive downlink telemetry from and send uplink telemetry to external device 24 with the aid of an antenna, which may be internal and/or external.

The various components of IMD 16 may be coupled to a power source such as battery 26. Battery 26 may be a lithium primary battery or lithium secondary (rechargeable) battery although other types of battery chemistries are contemplated. Battery 26 may be capable of holding a charge for several years. In general, battery 26 may supply power to one or more electrical components of IMD 16, such as, e.g., the signal generation circuitry, to allow IMD 16 to deliver therapy to patient 12, e.g., in the form of monitoring one or more patient parameters, delivery of electrical stimulation, or delivery on a therapeutic drug fluid. Battery 26 may include a lithium-containing anode and cathode including an active material that electrochemically reacts with the lithium within an electrolyte to generate power. A wide variety of battery types and Leads 18, 20, 22 that are coupled to IMD 16 may extend into the heart 14 of patient 12 to sense electrical activity of heart 14 and/or deliver electrical therapy to heart 14. In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 14. Right atrial (RA) lead 22 extends through one or more veins and the vena cava, and into the right atrium 30 of heart 14. In other examples, IMD 16 may deliver therapy to heart 14 from an extravascular tissue site in addition to or instead of delivering therapy via electrodes of intravascular leads 18, 20, 22. In the illustrated example, there are no electrodes located in left atrium 36. However, other examples may include electrodes in left atrium 36.

IMD 16 may sense electrical signals attendant to the depolarization and repolarization of heart 14 (e.g., cardiac signals) via electrodes (not shown in FIG. 1) coupled to at least one of the leads 18, 20, and 22. In some examples, IMD 16 provides pacing pulses to heart 14 based on the cardiac signals sensed within heart 14. The configurations of electrodes used by IMD 16 for sensing and pacing may be unipolar or bipolar. IMD 16 may also deliver defibrillation therapy and/or cardioversion therapy via electrodes located on at least one of the leads 18, 20, and 22. IMD 16 may detect arrhythmia of heart 14, such as fibrillation of ventricles 32 and 36, and deliver defibrillation therapy to heart 14 in the form of electrical shocks. In some examples, IMD 16 may be programmed to deliver a progression of therapies (e.g., shocks with increasing energy levels), until a fibrillation of heart 14 is stopped. IMD 16 may detect fibrillation by employing one or more fibrillation detection techniques known in the art. For example, IMD 16 may identify cardiac parameters of the cardiac signal (e.g., R-waves, and detect fibrillation based on the identified cardiac parameters).

In some examples, external device 24 may be a handheld computing device or a computer workstation. External device 24 may include a user interface that receives input from a user. The user interface may include, for example, a keypad and a display, which may be, for example, a cathode ray tube (CRT) display, a liquid crystal display (LCD) or light emitting diode (LED) display. The keypad may take the form of an alphanumeric keypad or a reduced set of keys associated with particular functions. External 24 can additionally or alternatively include a peripheral pointing device, such as a mouse, via which a user may interact with the user interface. In some embodiments, a display of external 24 may include a touch screen display, and a user may interact with programmer 24 via the display.

A user, such as a physician, technician, other clinician or caregiver, or the patient, may interact with external device 24 to communicate with IMD 16. For example, the user may interact with external device 24 to retrieve physiological or diagnostic information from IMD 16. A user may also interact with external device 24 to program IMD 16 (e.g., select values for operational parameters of IMD 16).

External device 24 may communicate with IMD 16 via wireless communication using any techniques known in the art. Examples of communication techniques may include, for example, low frequency or radiofrequency (RF) telemetry, but other techniques are also contemplated. In some examples, external device 24 may include a communication head that may be placed proximate to the patient's body near the IMD 16 implant site in order to improve the quality or security of communication between IMD 16 and external device 24.

In the example depicted in FIG. 1, IMD 16 is connected (or "coupled") to leads 18, 20, and 22. In the example, leads 18, 20, and 22 are connected to IMD 16 using the connector block 27. For example, leads 18, 20, and 22 are connected to IMD 16 using the lead connector ports in connector block 27. Once connected, leads 18, 20, and 22 are in electrical contact with the internal circuitry of IMD 16. Battery 26 may be positioned within the housing 40 of IMD 16. IMD housing 40 may be hermetically sealed and biologically inert. In some examples, housing 40 may be formed from a conductive material. For example, IMD housing 40 may be formed from a material including, but not limited to, titanium, stainless steel, among others.

Figure 2:
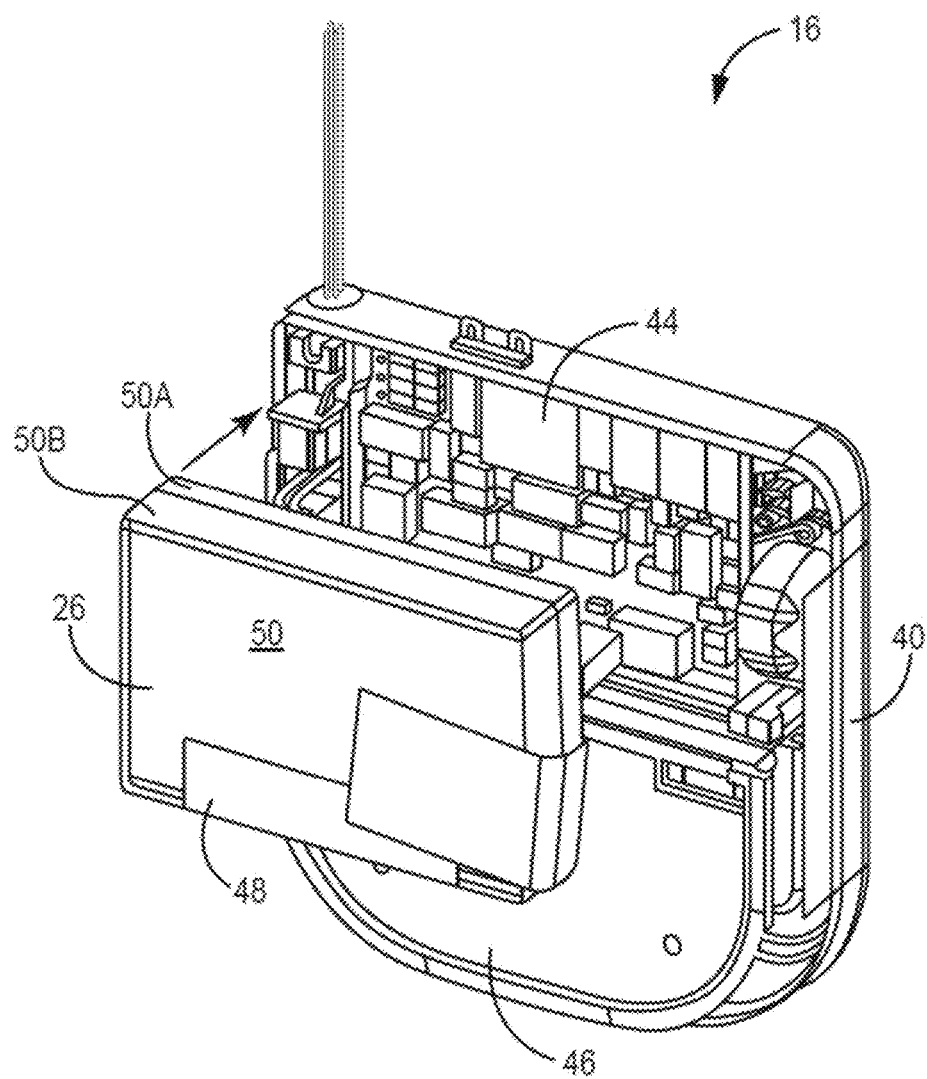
FIG. 2 is a conceptual diagram illustrating a partial exploded view of the implantable medical device (IMD) of FIG. 1.

FIG. 2 is a conceptual diagram of IMD 16 of FIG. 1 with connector block 27 not shown and a portion of housing 40 removed to illustrate some of the internal components within housing 40. IMD 16 includes housing 40, a control circuitry 44 (which may include processing circuitry), battery 26 (e.g., an organic electrolyte battery) and capacitor(s) 46. Control circuitry 44 may be configured to control one or more sensing and/or therapy delivery processes from IMD 16 via leads 18, 20, and 22 (not shown in FIG. 2). Battery 26 includes battery assembly housing 50 and insulator 48 (or liner) disposed therearound. Battery 26 charges capacitor(s) 46 and powers control circuitry 44.

Figure 3:
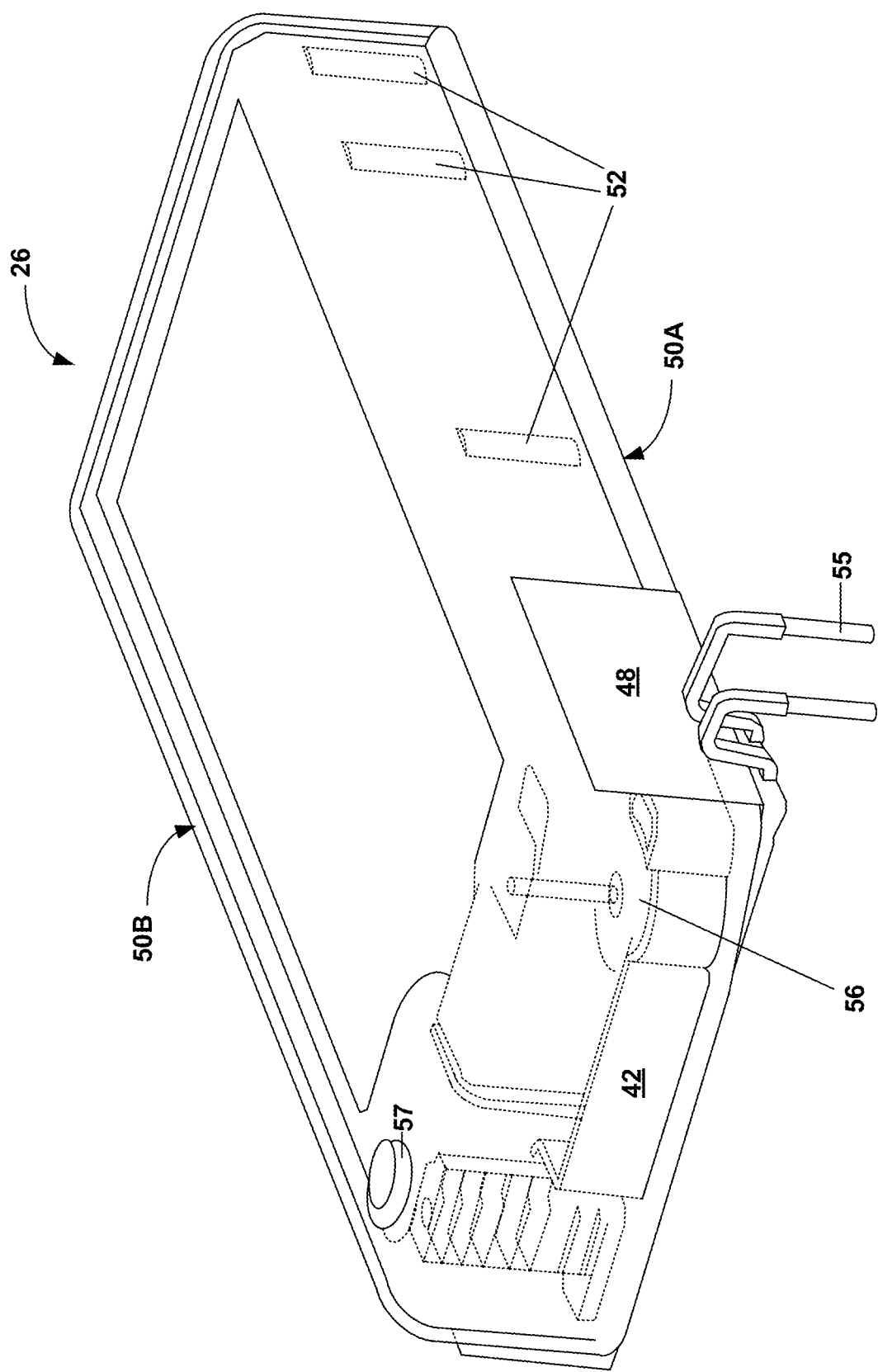
FIG. 3 is a perspective view of an example battery assembly for the IMD of FIG. 2.
Figure 4:
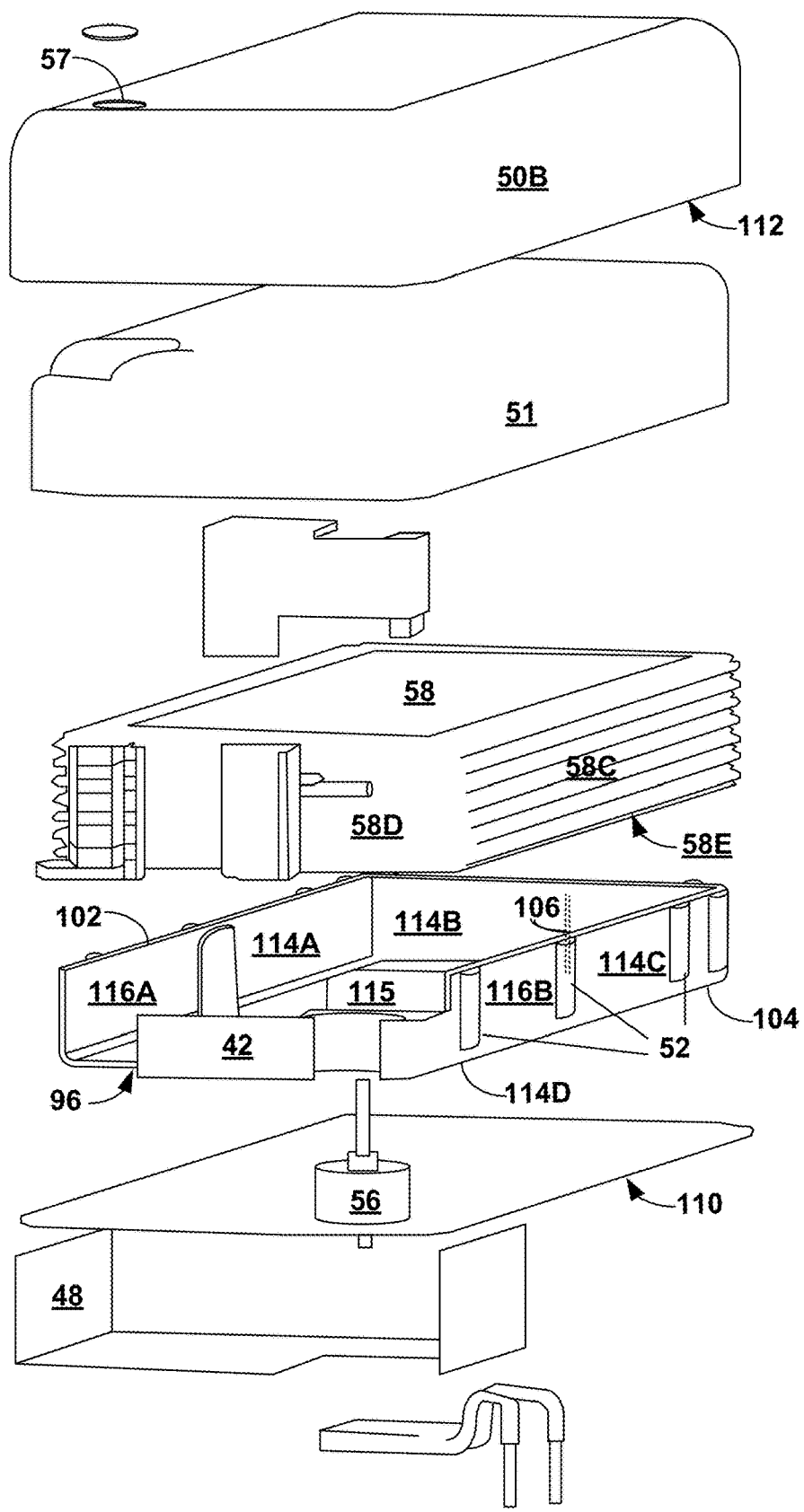
FIG. 4 is an exploded view of the example battery assembly of FIG. 3.

FIG. 3 is a perspective view, and FIG. 4 is an exploded view, of an example battery assembly 26 for the IMD of FIG. 2. As shown in FIGS. 3 and 4, battery 26 may include an external housing 50 having a bottom portion 50A and a top portion 50B, an electrical connector 55, an external battery insulator 48, a feed-through terminal 56, an electrode assembly 58, an intermediate member 42, and in some examples, a case liner 51.

Connector 55 includes a pair of conductors configured to transfer electrical energy from battery 26 into IMD 16. As detailed further below with respect to FIGS. 5 and 6, electrode assembly 58 may include a stacked assembly. For example, electrode assembly 58 may include a plurality of anode plates and a plurality of cathode plates in a stacked configuration, e.g., a stack of plates alternating between anode and cathode plates. The anode(s) comprise a set of electrode plates with a set of tabs extending therefrom that are conductively coupled to each other, e.g., directly or via a conductive coupler. Although not labeled, one or more spacers may be located between respective tabs. The conductive coupler may be a pin that extends vertically through the set of tabs and spacers located between respective tabs. Additionally, or alternatively, one or more side welds may also conductively and/or mechanically couple the set of tabs and spacers. In some examples, the conductive coupler may be a rivet that extends vertically through set of tabs and spacers that also mechanically attaches the individual tabs and spacers to each other. Examples of electrode stack 58 are described further in commonly assigned U.S. Provisional Patent Application No. 62/835,738 filed on Apr. 18, 2019; U.S. patent application Ser. No. 16/426,849 filed May 30, 2019; and U.S. patent application Ser. No. 16/530,470 filed Aug. 2, 2019, all of which are incorporated herein by reference.

Housing 50 includes bottom housing portion 50A and top housing portion 50B. The top and/or bottom housing portions may be composed of a metallic or alloy material, such as titanium, aluminum, stainless steel, copper, nickel, and alloys thereof. In some examples, the top and/or bottom housing portions may be composed of a weldable polymer. In some examples, housing 50 may define a thickness of between about 0.005 inches and 0.040 inches, such as between about 0.008 and about 0.016 inches. The material of housing 50 may be configured such that a weld joint may be formed between housing portions 50A and 50B. For example, during an assembly process, top housing portion 50B may be welded onto bottom housing portion 50A. For example, an outer edge or rim 110 (FIG. 4) of bottom housing portion 50A may be welded to a bottom edge or rim 112 of top housing portion 50B. In some examples, the weld may form a hermetic seal between bottom housing portion 50A and top housing portion 50B. In other examples, the weld need only form a fluid-tight seal so as to contain a fluid electrolyte within the internal cavity of housing 50.

During the welding process, heat energy may be transferred from housing portions 50 into any other component in conductive thermal contact (e.g., physical contact) with housing portions 50. Accordingly, in some examples in accordance with this disclosure, battery assembly 26 includes intermediate member 42 disposed in between housing 50 and electrode stack 58. Intermediate member 42 includes a structure configured to electrically and thermally insulate electrode stack 58 from housing 50. Additionally or alternatively, intermediate member 42 may be configured to position or align electrode stack 58 within housing 50, for example, to prevent electrode stack 58 from moving around inside housing 50.

In some examples, intermediate member 42 may include a generally rectangular-prism shape, for example, having a rectangular cross-sectional area composed of at least three side walls 114A-11C (FIG. 5) surrounding an internal cavity 115. The three side walls may each define an interior surface 116A and an exterior surface 116B. The internal cavity 115 may be substantially the same size and shape as electrode stack 58, such that the three side walls 114A-114C may be configured to surround electrode stack 58 when electrode stack 58 is placed within internal cavity 115. In some examples, in addition to three side walls 114A-114C, intermediate member 42 may include a bottom wall 114D (FIG. 4). In some examples, each of sidewalls 114A-114C and bottom wall 114D may generally define a thickness between about 0.005 inches and about 0.015 inches.

In some examples, intermediate member 42 may be composed of a thermally and electrically insulating material. The material may be injection moldable, machinable, or thermoformable. In some examples, the material may also be non-porous, chemically stable, and relatively lightweight. For example, intermediate member 42 may include a polymeric material, such as a plastic, and may in some examples be injection-molded. Examples of plastic materials for intermediate member 42 may include polypropylene and polyethylene. In some examples, intermediate member 42 may be composed of a ceramic.

In some examples in accordance with this disclosure, an external surface 116B of the side walls 114A-114C of intermediate member 42 may define a plurality of protrusions 52. Protrusions 52 may be configured to contact an interior surface of top portion 50B of external battery housing 50, or alternatively, an interior surface of case liner 51 (e.g., in examples which include case liner 51 as an internal layer of housing 50). For example, case liner 51 may include an additional layer of electrically insulating material between external housing 50 and electrode stack 58. In some examples, case liner 51 may be composed of a polymer or other thermally and/or electrically insulating material. In some examples, case liner 51 may be thermoformed or injection molded.

Protrusions 52 may be configured to perform a number of functions providing a number of advantages. For example, by physically contacting the interior surface of housing 50, protrusions 52 may firmly hold electrode stack 58 in place with respect to the top housing portion 50B, for example, to prevent electrode stack 58 from moving around within housing 50. By including periodic protrusions 52 to physically contact housing 50 and/or case liner 51, the rest of alignment member 42 may remain relatively thin, thereby reducing the cost of materials during production.

Additionally, protrusions 52 may be configured to absorb an amount of heat received from housing 50 while bottom housing portion 50A is welded onto top housing portion 50A, in order to prevent the rest of intermediate member 42 from absorbing the heat and structurally deforming (e.g., by melting of the material). In some examples, protrusions 52 may be considered "sacrificial," in that they may be configured to at least partially deform (e.g., melt) in response to receiving heat from housing 50 during the welding process.

In some examples, protrusions 52 may be composed of the same material (e.g., a polymeric material) as the rest of intermediate member 42. For example, intermediate member 42 may be injection molded so as to include protrusions 52, e.g., as a single component having the same composition throughout the component. In some examples, the inclusion of protrusions 52 may improve the accuracy or reduce the duration of the injection-molding process of intermediate member 42. For example, during the injection-molding process, protrusions 52 may function as molten-plastic supply pathways, enabling the molten plastic to access and fill other fine or narrow regions of intermediate member 42.

In other examples, protrusions 52 may be composed of a different material than the rest of intermediate member 42. For example, protrusions 52 may be composed of a ceramic material or other material having a relatively low thermal conductivity (e.g., a different thermal conductivity from the rest of side walls 114A-114C), so as to absorb a relatively large amount of heat from housing 50 without substantially deforming. In some examples, protrusions 52 may be composed of a metal, such as in examples in which protrusions 52 are electrically insulated from electrode stack 58 by side walls 114. In some examples, protrusions 52 may be inserted into the molding for intermediate member 42 (e.g., intermediate member 42 may be insertion molded). In other examples, protrusions 52 may be rigidly coupled (e.g., adhered) or otherwise inserted into intermediate member 42 after intermediate member 42 has been formed.

In the examples depicted in FIGS. 3 and 4, each of protrusions 52 includes a shape that is generally semi-cylindrical, however, protrusions 52 may take the form of any suitable geometric shape that achieves the intended functions of protrusions 52. As shown in FIG. 4, each of protrusions 52 may be shaped so as to define a central longitudinal axis 106. In some examples, each of protrusions 52 may be substantially aligned such that all of their central longitudinal axes 106 are parallel to one another. Protrusions 52 may extend from a top edge 102 of the respective side wall 114 of intermediate member 42 down toward a bottom edge 104 of the side wall of intermediate member 42. In some examples, one or more of protrusions 52 may extend substantially all the way from top edge 102 of the side wall 114 of intermediate member 42 to bottom edge 104, while in other examples, one or more of protrusions 52 may extend only a portion of the distance between top edge 102 and bottom edge 104. In some examples, protrusions 52 may stop before fully reaching the bottom edge 104, so as to prevent any melted or deformed material of protrusions 52 from entering the weld joint between top housing portion 50B and bottom housing portion 50A.

In another example not depicted in FIG. 4, one or more protrusions may be oriented such that their longitudinal axes 106 may be parallel to top edge 102 and to bottom edge 104 of intermediate member 42, such that the protrusions may extend circumferentially around the perimeter of the exterior surface 116B of side walls 114A-114C of intermediate member 42.

Figure 5:
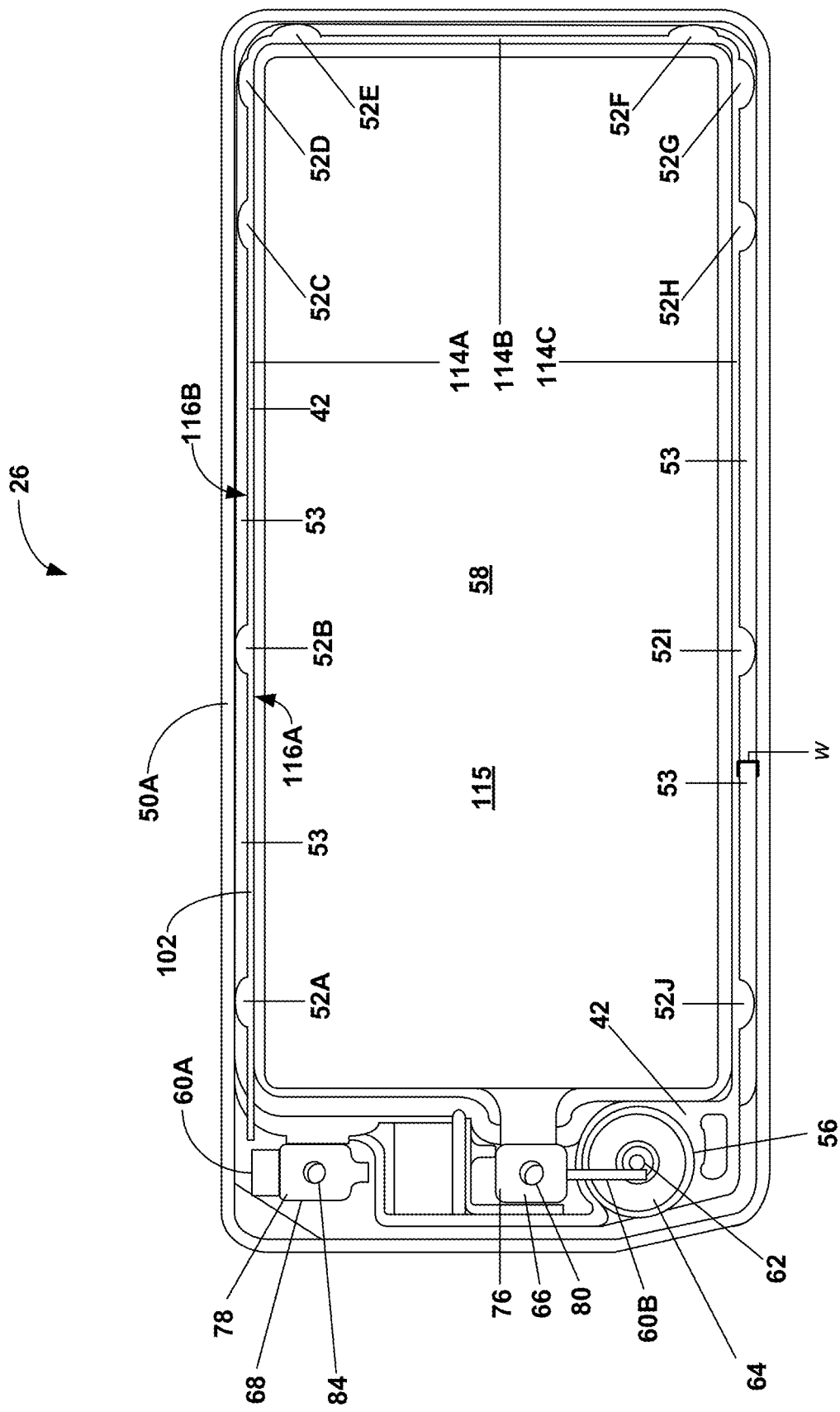
FIG. 5 is a cross-sectional view.
Figure 6:
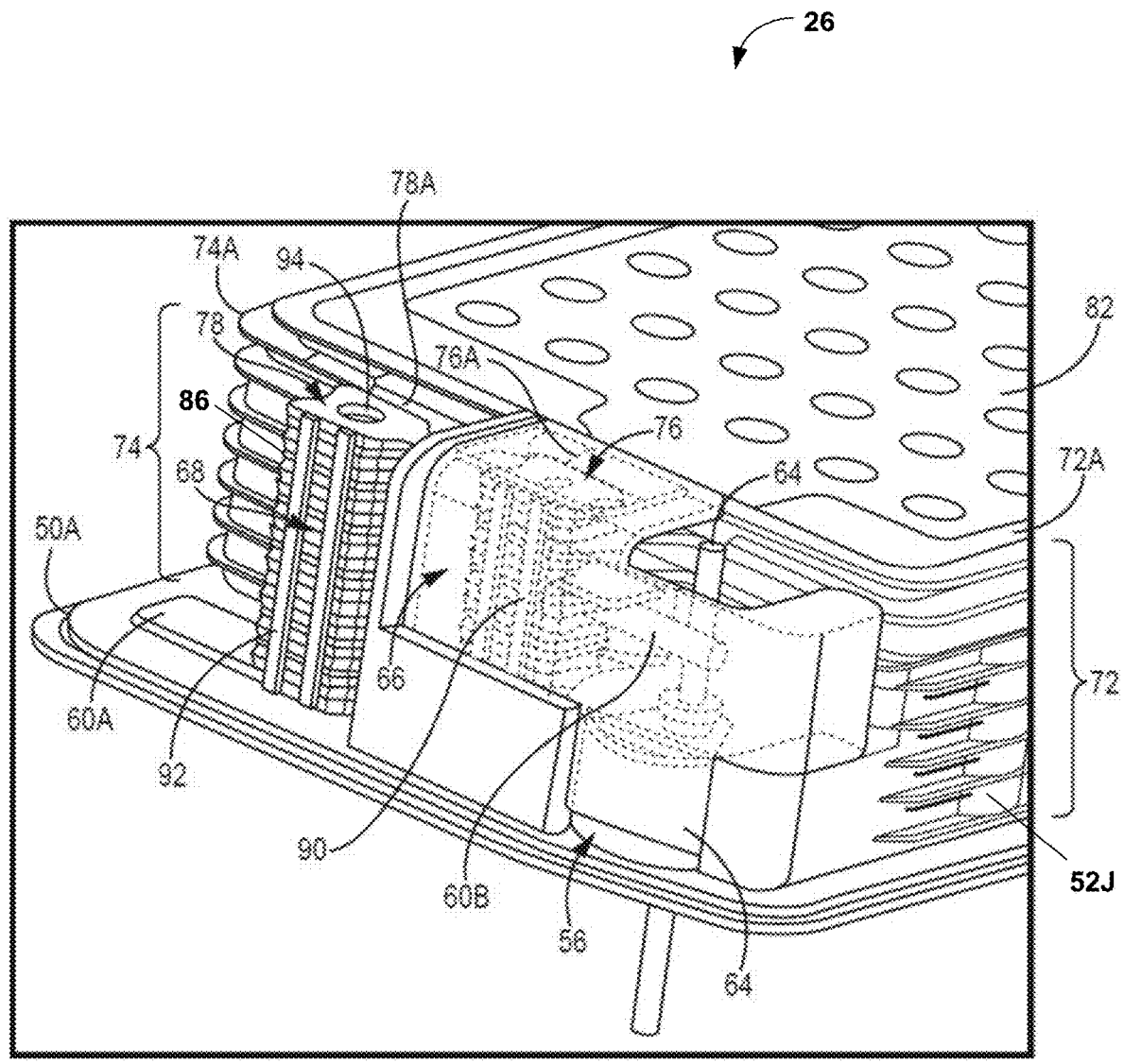
FIG. 6 is a perspective view, of a portion of the example battery assembly of FIGS. 3 and 4.

FIG. 5 is a cross-sectional view, and FIG. 6 is a conceptual diagram, illustrating aspects of the example battery assembly 26 of FIGS. 3 and 4. Specifically, FIG. 5 shows an overhead view of the top edge 102 of the side walls 114A-114C of intermediate member 42. In the example shown in FIG. 5, intermediate member 42 includes ten protrusions 52A-52J extending outward from the exterior surface 116B of side walls 114A-114C. However, in other examples, intermediate member 42 may include more or fewer protrusions 52. Protrusions 52 may be evenly spaced or unevenly spaced around the circumference of exterior surface 116B of intermediate member 42.

As shown in FIG. 5, each pair of consecutive protrusions 52 defines a corresponding insulation gap 53 between them. Insulation gaps 53 are configured to thermally insulate intermediate member 42 from housing 50 while top housing portion 50B (FIG. 4) is welded onto bottom housing portion 50A during the assembly process. For example, gaps 53 may include an open or void space in between the interior surface of housing 50 and the exterior surface 116B of alignment member 42. Gaps 53 may help reduce the conduction of heat from housing 50 to alignment member 42 in the regions immediately surrounding the respective gap 53, as compared to example regions in which alignment member 42 is in direct thermal contact with the interior surface of housing 50. Insulation gaps 53 may each define a respective gap width "w" equal to a width of the respective protrusions 52, e.g., a distance that each of the protrusions 52 extends from the exterior surface 116B of the respective side wall 114. In some examples, width w of protrusions 52 and gaps 53 may be between approximately 0.005 inches and 0.025 inches.

In some examples, some protrusions 52 may extend a distance w from the respective sidewall 114 that is different from the width w of other protrusions 52. For example, in some scenarios, the shape of intermediate member 42 may be different from the shape of housing 50. Accordingly, protrusions 52 on side walls 114A and 114C may have a different width w from protrusions on side wall 114B, as one example.

In some examples, an electrolyte may be filled into electrode assembly 58 and gaps 53 via a fill port 57 (FIG. 4) in housing 50. The electrolyte creates an ionic path (e.g., a medium for migration of ions) between the anode(s) and the cathode(s) of electrode assembly 58 during an electrochemical reaction with these electrodes. The electrolyte serves as a medium for migration of ions between the anode(s) and the cathode(s) during an electrochemical reaction with these electrodes.

Housing 50 houses electrode assembly 58 with the electrolyte. Top portion 50B and bottom portion 50A of housing may be welded or otherwise attached to seal the enclosed components of battery 26 within housing 50. Feed-through assembly 56, formed by pin 62 and insulator member/ferrule 64, is electrically connected to jumper pin 60B. The connection between pin 62 and jumper pin 60B allows delivery of positive charge from electrode assembly 58 to electronic components outside of battery 26.

In the example shown in FIG. 6, electrode assembly 58 is depicted as a stacked assembly. The anode(s) comprise a set of electrode plates 72 (including individual anode electrode plate 76A) with a set of tabs 76 (including individual tab 76A) extending therefrom that are conductively coupled via a conductive coupler 80 (FIG. 5) (also referred to as an anode collector). Although not labeled, the one or more spacers (e.g., conductive spacers) may be located between respective tabs in the set of tabs 76. The conductive coupler 80 may be a pin that extends vertically through the set of tabs 76 and spacers located between respective tabs. Additionally, or alternatively, one or more welds 90 may also conductively couple the set of tabs 76 and spacers. In accordance with at least some of examples of the disclosure, as described below, conductive coupler 80 may be a rivet that extends vertically through set of tabs 76 and spacers that also mechanically attaches the individual tabs 76 and spacers to each other.

Each anode electrode plate 72A includes a current collector or grid 82, a tab 76A extending therefrom, and an electrode material. The electrode material (or anode material) may include elements from Group IA, IIA or IIIB of the periodic table of elements (e.g. lithium, sodium, potassium, etc.), alloys thereof, intermetallic compounds (e.g. Li—Si, Li—B, Li—Si—B etc.), or an alkali metal (e.g. lithium, etc.) in metallic form.

Cathode tabs 68 may be constructed in a similar manner as anode tabs 66. The cathodes include a set of electrode plates 74 (including individual cathode electrode plates 74A) with a set of tabs 78 (including individual tab 78A) extending therefrom. As labelled in FIG. 6, e.g., one or more spacers (e.g., conductive spacers 86) may be located between respective tabs in the set of tabs 78. The conductive coupler 84 connects the set of tabs 78 and spacers 86. Conductive coupler 84 or other cathode collector may be connected to conductive member 60A. Conductive member 60A, shaped as a spacer plate, may comprise titanium, aluminum/titanium clad metal or other suitable materials. Conductive member 60A allows cathode tabs 68 to be electrically coupled to electronic components outside of battery 26. Each tab of the set of tabs 78 (including, e.g., individual tab 78A) may be additionally, or alternatively, attached to each other via laser weld(s) 92. Each cathode electrode plate 74A includes a current collector (not shown) or grid, an electrode material and a tab 78A extending therefrom. Tab 78A comprises conductive material (e.g., aluminum, etc.). Tab 78A comprises a conductive material (e.g., copper, titanium, aluminum, etc.). Electrode material (or cathode material) may include metal oxides (e.g., vanadium oxide, silver vanadium oxide (SVO), manganese dioxide, etc.), carbon monofluoride and hybrids thereof (e.g., $CFx+MnO_2$), combination silver vanadium oxide (CSVO), lithium ion, other rechargeable chemistries, or other suitable compounds.

Figure 7A:
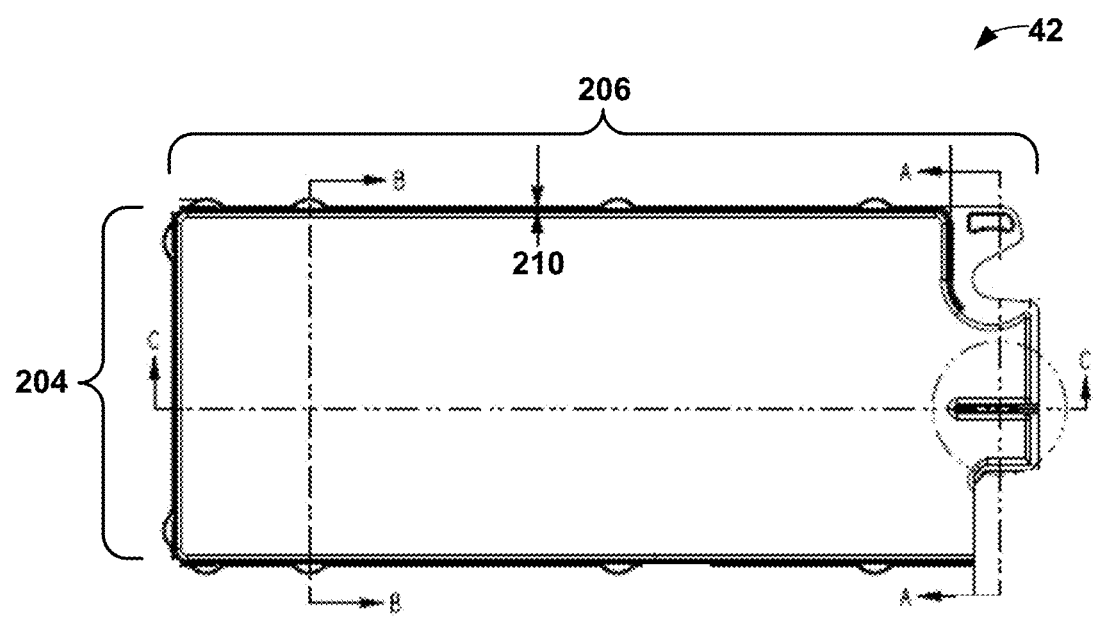
FIG. 7A is a schematic diagram depicting an overhead view of an intermediate member for a battery assembly, in accordance with examples of this disclosure.
Figure 7B:
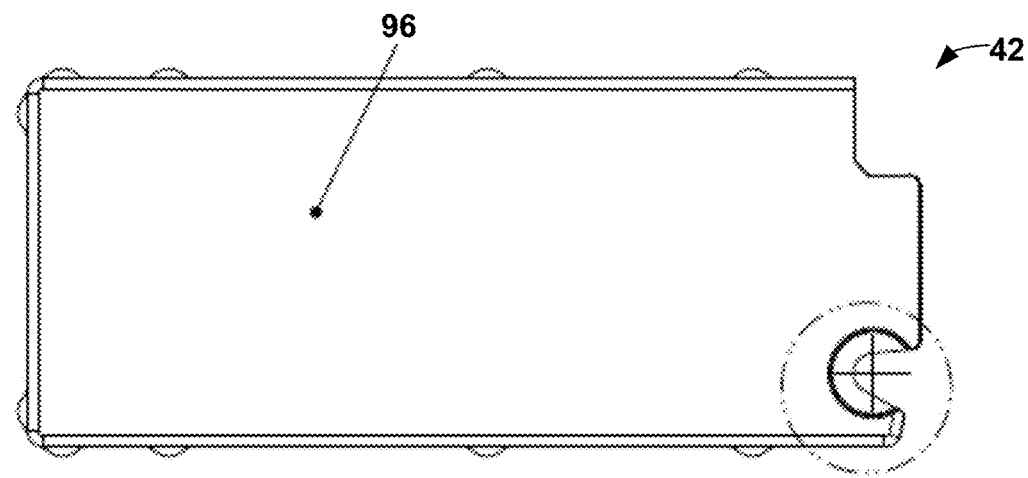
FIG. 7B is a schematic diagram depicting an underside of an intermediate member for a battery assembly, in accordance with examples of this disclosure.

FIGS. 7A and 7B are diagrams illustrating an example of intermediate member 42 of FIGS. 3-6. In particular, FIG. 7A depicts an overhead view of intermediate member 42, and FIG. 7B depicts an underside 96 of intermediate member 42. FIGS. 8A-8C are cross-sectional views of intermediate member 42 of FIGS. 7A and 7B. In particular, FIG. 8A is a cross-sectional view through line A-A of FIG. 7A. FIG. 8B is a cross-sectional view through line B-B of FIG. 7A. FIG. 8C is a cross-sectional view through line C-C of FIG. 7A.

As shown in FIGS. 7A-8C, intermediate member 42 may define a width 204 of between about 0.1 inches and about 2.0 inches. Intermediate member 42 may define a length 206 of between about 1.0 inch and about 3.0 inches. Intermediate member 42 may define a height 208 of between about 0.10 inches and about 1.0 inch. Side walls 114A-114C may define a thickness 210 of between about 0.001 and about 0.1 inches. Bottom wall 114D of intermediate member 42 may include a thickness 202 of between about 0.001 and about 0.05 inches. Other values are contemplated.

Figure 9A:
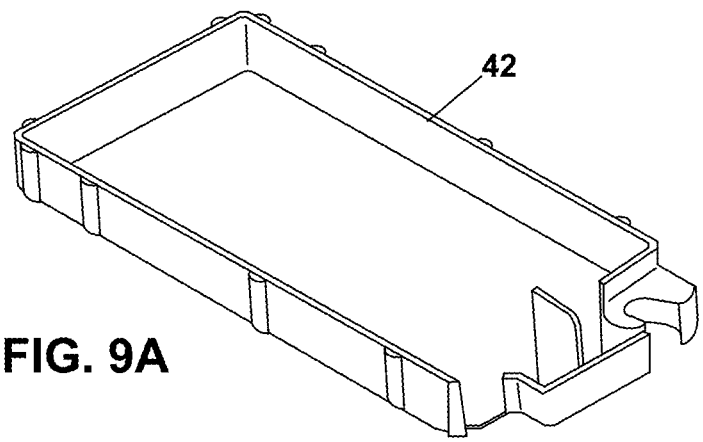
FIGS. 9A-9C are perspective views depicting various angles of an intermediate member for a battery assembly, in accordance with examples of this disclosure.
Figure 9B:
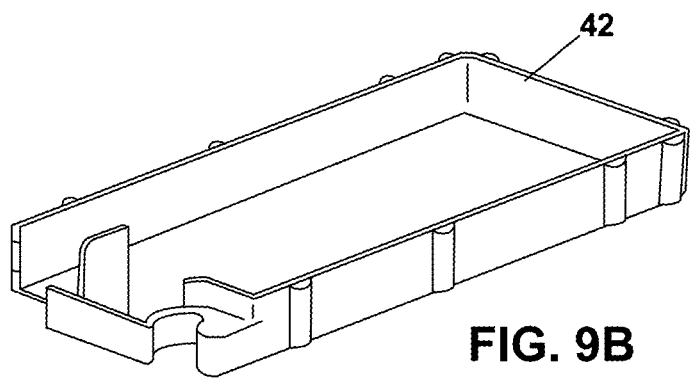
Figure 9C:
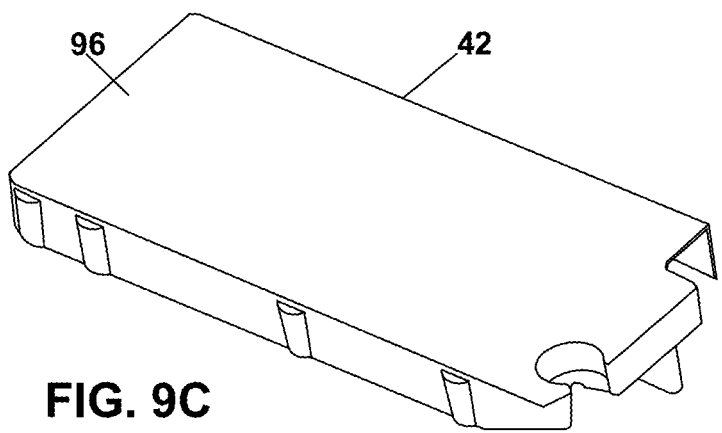

FIGS. 9A-9C are perspective views depicting various angles of an example intermediate member for a battery assembly, in accordance with examples of this disclosure. In particular, FIGS. 9A and 9B depict a top side of intermediate member 42. FIG. 9C depicts an underside 96 of intermediate member 42. For example, underside 96 may be configured to contact bottom housing portion 50A of FIG. 4.

Figure 10:
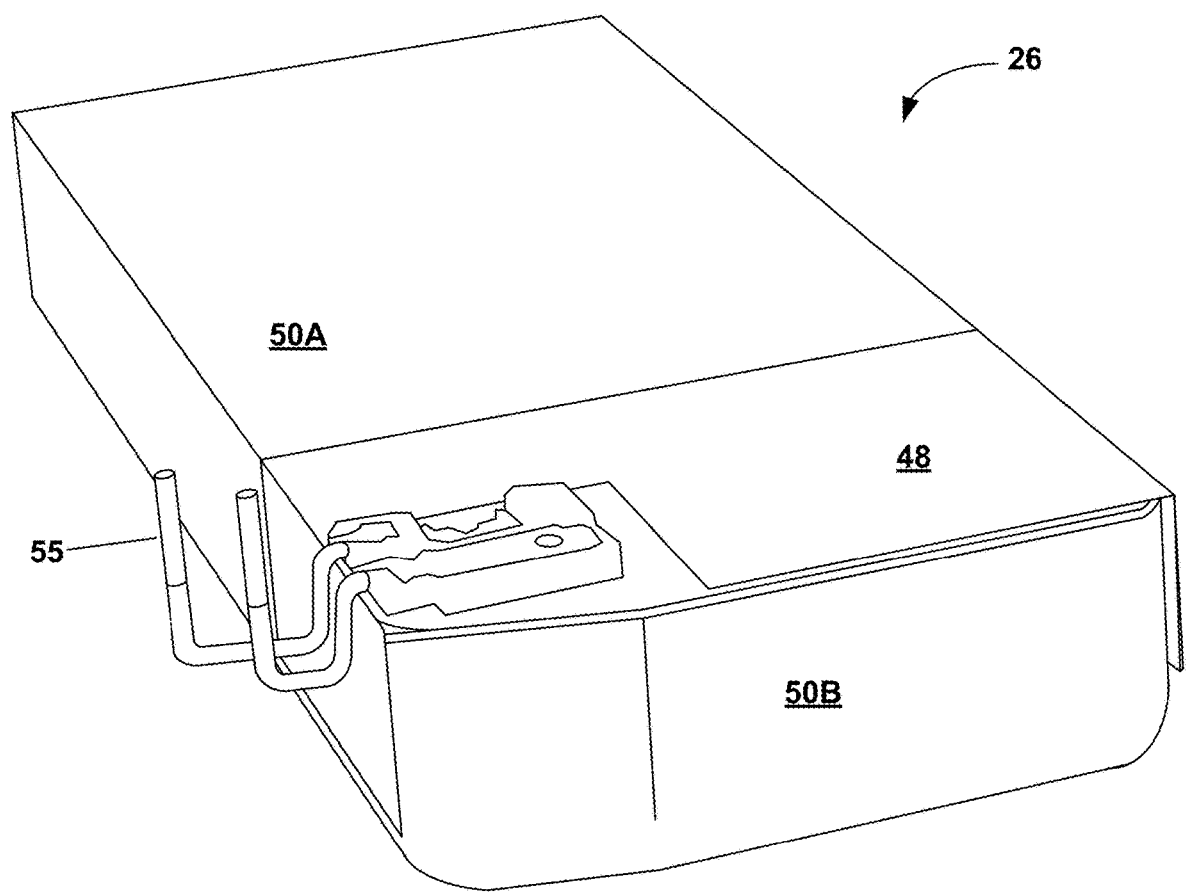
FIG. 10 is a perspective view of a battery assembly for an IMD, in accordance with some techniques of this disclosure.

FIG. 10 is a perspective view of a battery assembly for an IMD in accordance with some techniques of this disclosure. More specifically, FIG. 10 depicts an underside of battery assembly 26, including bottom housing portion 50A and top housing portion 50B. In the example configuration depicted in FIG. 10, bottom housing portion 50A functions as a planar lid to box-shaped top housing portion 50B. In other examples, top housing portion 50B and bottom housing portion 50A may take the form of a "clamshell" configuration, wherein both portions are approximately equal in size and shape, and accordingly align at a depth approximately halfway through the thickness of battery 26.

Figure 11:
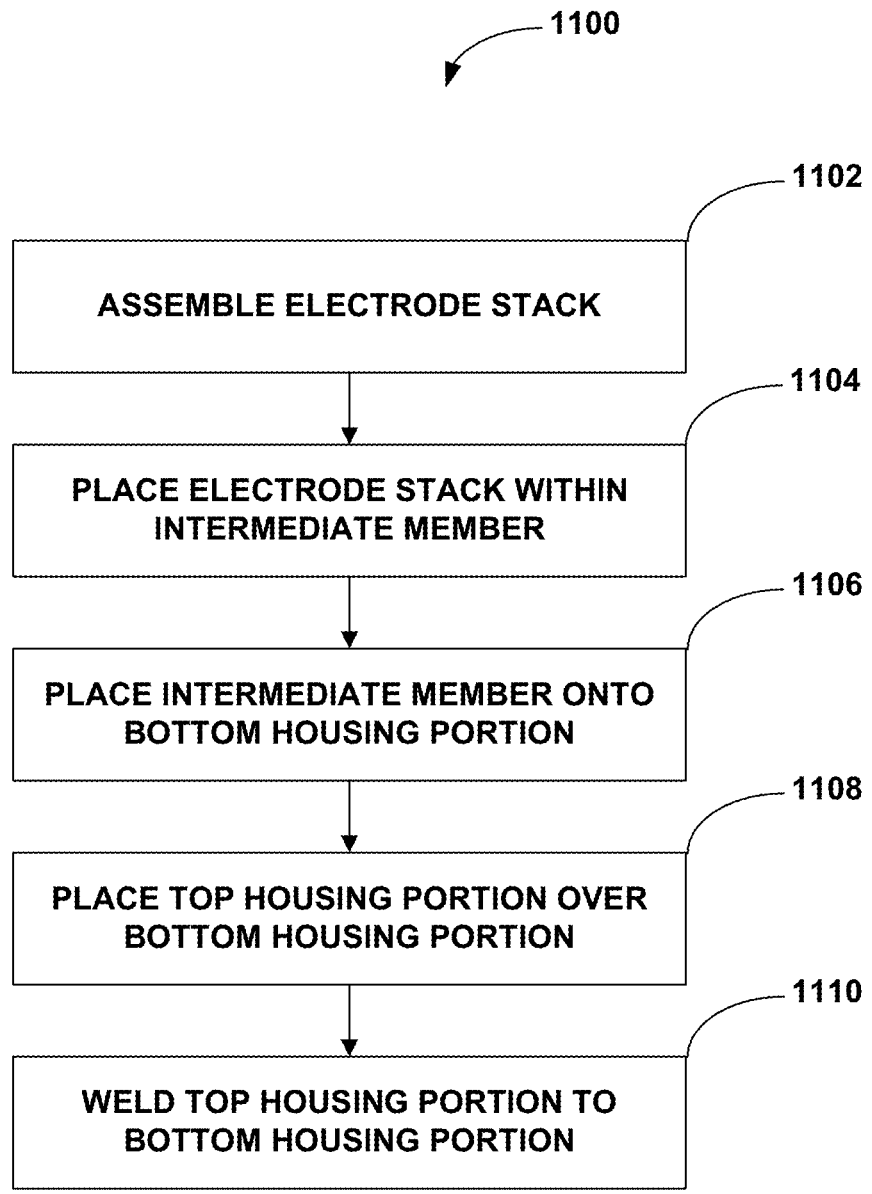
FIG. 11 is a flow diagram depicting an example method of assembling a battery for an IMD, in accordance with techniques of this disclosure.

FIG. 11 is a flow diagram depicting an example method 1100 of assembling a battery for an IMD, in accordance with techniques of this disclosure. Method 1100 is primarily described with respect to battery assembly 26 of FIGS. 1-6, however the techniques may be applicable to any battery assembly having one or more protrusions configured to perform the functions described. A plurality of anode and cathode plates may be assembled into an electrode stack 58 (1102). The electrode stack 58 may be placed within an internal cavity 115 of intermediate member 42 (1104). Intermediate member 42 with electrode stack 58 may be placed on top of a bottom housing portion 50A of a battery housing 50 (1106). A top housing portion 50B of battery housing 50 may be placed over top of intermediate member 42 such that one or more protrusions 52 extending from an exterior surface 116B of intermediate member 42 contact an interior surface of top housing portion 50B (1108). A bottom edge 112 of top housing portion 50B may be welded, such as laser welded, to an outer edge 110 of bottom housing portion 50A (1110). In some examples, the heat from the welding process may be transferred onto the protrusions 52 extending from intermediate member 42. In some examples, the protrusions 52 may partially deform in response to receiving the heat, sacrificing some of their own structure but simultaneously insulating the more heat-sensitive electrode stack 58 within intermediate member 42.

The following numbered clauses provide some examples of the disclosure.

Clause 1: In some examples, a battery assembly that includes: a housing; an electrode stack including a plurality of electrode plates disposed inside the housing; and an intermediate member configured to align the electrode stack at a fixed position within the housing, the intermediate member including a plurality of side walls and at least one protrusion disposed on an exterior surface of the plurality of side walls, wherein the at least one protrusion is in thermal contact with an interior surface of the housing.

Clause 2: In some examples of the battery assembly of clause 1, the at least one protrusion defines at least one respective insulation gap between the intermediate member and the housing.

Clause 3: In some examples of the battery assembly of clause 2, the at least one respective insulation gap is filled with an electrolyte.

Clause 4: In some examples of the battery assembly of any of clauses 1-3, the at least one protrusion is configured to at least partially deform in response to receiving heat transferred from the interior surface of the housing.

Clause 5: In some examples of the battery assembly of any of clauses 1-4, the intermediate member includes a polymeric material.

Clause 6: In some examples of the battery assembly of any of clauses 1-5, the intermediate member is injection-molded.

Clause 7: In some examples of the battery assembly of any of clauses 1-6, the at least one protrusion includes a plurality of protrusions, each protrusion of the plurality including a generally semi-cylindrical shape defining a longitudinal axis, wherein the longitudinal axes of the plurality of protrusions are substantially parallel to each other.

Clause 8: In some examples of the battery assembly of any of clauses 1-7, the at least one protrusion includes a same material as the intermediate member.

Clause 9: In some examples of the battery assembly of any of clauses 1-8, the at least one protrusion includes a ceramic material.

Clause 10: In some examples of the battery assembly of any of clauses 1-9, the intermediate member is insertion-molded.

Clause 11: In some examples of the battery assembly of any of clauses 1-10, the intermediate member includes ten protrusions disposed on the exterior surface of the side walls.

Clause 12: In some examples of the battery assembly of any of clauses 1-11, the side walls of the intermediate member define a top edge and a bottom edge, wherein the at least one protrusion extends from the top edge toward the bottom edge.

Clause 13: In some examples of the battery assembly of clause 12, the at least one protrusion does not extend entirely to the bottom edge of the intermediate member.

Clause 14: In some examples of the battery assembly of any of clauses 1-11, the side walls of the intermediate member define a top edge and a bottom edge, wherein the at least one protrusion extends circumferentially around the side walls and parallel to the top edge and to the bottom edge.

Clause 15: In some examples, an implantable medical device (IMD) includes: an outer housing; processing circuitry; and a battery assembly within the outer housing, the battery assembly including: a battery housing; an electrode stack comprising a plurality of electrode plates disposed inside the housing; and an intermediate member configured to align the electrode stack at a fixed position within the housing, the intermediate member including a plurality of side walls and at least one protrusion disposed on an exterior surface of the side walls; wherein the at least one protrusion is in thermal contact with an interior surface of the housing, and wherein the processing circuitry is configured to control delivery of electrical therapy from the implantable medical device to a patient using power supplied by the battery assembly.

Clause 16: In some examples of the IMD of clause 15, the at least one protrusion defines at least one respective insulation gap between the intermediate member and the battery housing.

Clause 17: In some examples of the IMD of clause 16, the at least one insulation gap is filled with an electrolyte.

Clause 18: In some examples of the IMD of any of clauses 15-17, the at least one protrusion is configured to at least partially deform in response to receiving heat transferred from the interior surface of the battery housing.

Clause 19: In some examples of the IMD of any of clauses 15-18, the intermediate member includes a polymeric material.

Clause 20: In some examples of the IMD of any of clauses 15-19, the intermediate member is injection-molded.

Clause 21: In some examples of the IMD of any of clauses 15-20, the at least one protrusion includes a plurality of protrusions, wherein each protrusion of the plurality of protrusions includes a generally semi-cylindrical shape defining a longitudinal axis, wherein the longitudinal axes of the plurality of protrusions are substantially parallel to each other.

Clause 22: In some examples of the IMD of any of clauses 15-21, the at least one protrusion includes a same material as the intermediate member.

Clause 23: In some examples of the IMD of any of clauses 15-22, the at least one protrusion comprises a ceramic material.

Clause 24: In some examples of the IMD of any of clauses 15-19 and 21-23, the intermediate member is insertion-molded.

Clause 25: In some examples of the IMD of any of clauses 15-24, the intermediate member includes ten protrusions disposed on the exterior surface of the side walls of the intermediate member.

Clause 26: In some examples of the IMD of any of clauses 15-25, the side walls of the intermediate member define a top edge and a bottom edge, wherein the at least one protrusion extends from the top edge toward the bottom edge.

Clause 27: In some examples of the IMD of clause 26, the at least one protrusion does not extend entirely to the bottom edge of the intermediate member.

Clause 28: In some examples of the IMD of any of clauses 15-25, the side walls of the intermediate member define a top edge and a bottom edge, wherein the at least one protrusion extends circumferentially around the side walls and parallel to the top edge and to the bottom edge.

Clause 29: In some examples, a method includes assembling the battery assembly of any one of clauses 1-28.

Various examples have been described in the disclosure. These and other examples are within the scope of the following claims.

The invention claimed is:

1. A battery assembly, the assembly comprising:
   a housing;
   an electrode stack comprising a plurality of electrode plates disposed inside the housing; and
   an intermediate member configured to align the electrode stack at a fixed position within the housing, the intermediate member comprising:
      a plurality of side walls; and
      a plurality of protrusions disposed on an exterior surface of the plurality of side walls,
      wherein the plurality of protrusions comprise a same material as the plurality of side walls and are formed together through injection-molding or insertion-molding as a single component with the plurality of side walls, and wherein at least one protrusion of the plurality of protrusions is in thermal contact with an interior surface of the housing, and
      wherein the side walls define a top edge and a bottom edge, wherein the at least one protrusion extends from the top edge toward the bottom edge, and wherein the at least one protrusion does not extend entirely to the bottom edge of the intermediate member.

2. The battery assembly of claim 1, wherein the at least one protrusion defines at least one respective insulation gap between the intermediate member and the housing.

3. The battery assembly of claim 2, wherein the at least one respective insulation gap is filled with an electrolyte.

4. The battery assembly of claim 1, wherein the at least one protrusion is configured to at least partially deform in response to receiving heat transferred from the interior surface of the housing.

5. The battery assembly of claim 1, wherein the plurality of side walls and the plurality of protrusions comprise a polymeric material.

6. The battery assembly of claim 1, wherein each protrusion of the plurality of protrusions comprises a generally semi-cylindrical shape defining a longitudinal axis, wherein the longitudinal axes of the plurality of protrusions are substantially parallel to each other.

7. The battery assembly of claim 1, wherein the plurality of side walls and the plurality of protrusions comprise a ceramic material.

8. The battery assembly of claim 1, wherein the at least one protrusion comprises a first at least one protrusion, and wherein a second at least one protrusion extends circumferentially around the side walls and parallel to the top edge and to the bottom edge.

9. An implantable medical device (IMD) comprising:
   an outer housing;
   processing circuitry; and
   a battery assembly within the outer housing, the battery assembly comprising:
      a battery housing;
      an electrode stack comprising a plurality of electrode plates disposed inside the housing; and
      an intermediate member configured to align the electrode stack at a fixed position within the housing, the intermediate member comprising:
         a plurality of side walls; and
         a plurality of protrusions disposed on an exterior surface of the plurality of side walls,
         wherein the plurality of protrusions comprise a same material as the plurality of side walls and are formed together through injection-molding or insertion-molding as a single component with the plurality of side walls, and wherein at least one protrusion of the plurality of protrusions is in thermal contact with an interior surface of the housing, and
         wherein the side walls define a top edge and a bottom edge, wherein the at least one protrusion extends from the top edge toward the bottom edge, and wherein the at least one protrusion does not extend entirely to the bottom edge of the intermediate member;
   wherein the processing circuitry is configured to control delivery of electrical therapy from the IMD to a patient using power supplied by the battery assembly.

10. The IMD of claim 9, wherein the at least one protrusion defines at least one respective insulation gap between the intermediate member and the battery housing.

11. The IMD of claim 10, wherein the at least one insulation gap is filled with an electrolyte.

12. The IMD of claim 9, wherein the at least one protrusion is configured to at least partially deform in response to receiving heat transferred from the interior surface of the battery housing.

13. The IMD of claim 9, wherein each protrusion of the plurality of protrusions comprises a generally semi-cylindrical shape defining a longitudinal axis, wherein the longitudinal axes of the plurality of protrusions are substantially parallel to each other.

14. The IMD of claim 9, wherein the plurality of side walls and the plurality of protrusions comprise a ceramic material.

15. The IMD of claim 9, wherein the at least one protrusion comprises a first at least one protrusion, and wherein a second at least one protrusion extends circumferentially around the side walls and parallel to the top edge and to the bottom edge.

* * * * *